(12) United States Patent
Nambirajan et al.

(10) Patent No.: US 11,545,248 B2
(45) Date of Patent: *Jan. 3, 2023

(54) MACHINE LEARNING SYSTEMS FOR PREDICTIVE MODELING AND RELATED METHODS

(71) Applicant: Express Scripts Strategic Development, Inc., St. Louis, MO (US)

(72) Inventors: Balakrishnan Nambirajan, Parsippany, NJ (US); Garret L. Anderson, Arden Hills, MN (US); Heather L. Durosko, New Castle, PA (US); Angela Gorbett, Alpharetta, GA (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 52 days.

This patent is subject to a terminal disclaimer.

(21) Appl. No.: 17/367,253

(22) Filed: Jul. 2, 2021

(65) Prior Publication Data

US 2021/0335470 A1 Oct. 28, 2021

Related U.S. Application Data

(63) Continuation of application No. 16/388,047, filed on Apr. 18, 2019, now Pat. No. 11,056,222.

(51) Int. Cl.
*G16H 20/10* (2018.01)
*G06F 16/901* (2019.01)
*G06F 17/18* (2006.01)
*G06N 20/00* (2019.01)

(52) U.S. Cl.
CPC ......... *G16H 20/10* (2018.01); *G06F 16/9027* (2019.01); *G06F 17/18* (2013.01); *G06N 20/00* (2019.01)

(58) Field of Classification Search
CPC .... G16H 20/10; G06N 20/00; G06F 16/9027; G06F 17/18
See application file for complete search history.

(56) References Cited

U.S. PATENT DOCUMENTS 6,519,534 B2   2/2003   Chen
7,912,698 B2   3/2011   Statnikov
(Continued)

OTHER PUBLICATIONS

Infinx Provides AI-Powered Payment Lifecycle Solutions for Healthcare Providers, Superb Crew Interviews (Feb. 11, 2019) (Year: 2019).*

(Continued)

*Primary Examiner* — Evangeline Barr
*Assistant Examiner* — Jordan L Jackson
(74) *Attorney, Agent, or Firm* — Stinson LLP

(57) ABSTRACT

A machine learning system for training a data model to predict data states in medical orders is described. The machine learning system is configured to train a data model to predict whether a medical order requires prior authorization ("PA") for medical orders within a medical order data set so that related systems may process incoming medical orders with PA determinations predicted by the data model. The machine learning system includes a first data warehouse system. The first prescription processing system generates a data model of historical orders and payer responses, apply a predictive machine learning model to the data model to generate a trained predictor of whether a medical order requires PA, associated with order data, apply the trained predictor to a plurality of production orders to determine PA for each of the plurality of production orders, and process the plurality of production orders with each associated PA determination.

20 Claims, 7 Drawing Sheets

(56) References Cited

U.S. PATENT DOCUMENTS

| | | | |
|---|---|---|---|
| 9,471,884 B2 | 10/2016 | Hamann | |
| 9,501,624 B2 | 11/2016 | Vishnubhatla | |
| 2010/0324929 A1* | 12/2010 | Petrasich | G06Q 10/00 |
| | | | 706/46 |
| 2012/0179478 A1 | 7/2012 | Ross | |
| 2017/0046491 A1* | 2/2017 | Scantland | G06Q 40/08 |
| 2017/0046492 A1* | 2/2017 | Renner | G16H 10/60 |
| 2018/0114139 A1 | 4/2018 | Kucera | |
| 2019/0080416 A1 | 3/2019 | Smith | |
| 2019/0102693 A1 | 4/2019 | Yates | |

OTHER PUBLICATIONS

Navaneeth Nair, AI-driven Software Provides Complete Prior Authorization Coverage for Healthcare Providers, The Healthcare Guys Healthcare IT (Feb. 9, 2019) (Year: 2019).*

Infinx Unveils New Prior Authorization Determination Engine, Cision PR Newswire (Jan. 30, 2019) (Year: 2019).*

Robert Rowley, Can AI Reduce The Prior Authorization Burden in Healthcare?, HIT Consultant (Jul. 11, 2016) (Year: 2016).*

Ron Wince, Why AI is the Future of Prior Auths, insideBigData White Paper Library Industry Segments: Healthcare (Dec. 21, 2018) (Year: 2018).*

Wince, Why AI is the Future of Prior Auths, Inside Big Data Industry Segments (Dec. 21, 2018) (Year: 2018).

Nair, AI-driven Software Provides Complete Prior Authorization Coverage for Healthcare Providers, The Healthcare Guys Healthcare IT (Feb. 9, 2019) (Year: 2019).

Rowley, Can AI Reduce the Prior Authorization Burden in Healthcare?, HIT Consul tant (Jul. 11, 2016) (Year: 2016).

* cited by examiner

MACHINE LEARNING SYSTEMS FOR PREDICTIVE MODELING AND RELATED METHODS

CROSS REFERENCE TO RELATED APPLICATION

This application is a continuation of U.S. patent application Ser. No. 16/388,047 Apr. 18, 2019, the entire disclosure of which is incorporated by reference.

FIELD OF INVENTION

The field relates to machine learning systems for predictive modeling. The machine learning systems are used identify characteristics associated with data sets, where the characteristics have relationships to the data sets that are unknown and unpredictable without the use of the disclosed machine learning systems. The field further relates to the use of such machine learning systems in high volume fulfillment centers that process medical orders, where the machine learning systems generate predictive models that determine whether a given medical order data set has a characteristic of prior authorization (PA).

BACKGROUND OF THE DISCLOSURE

The relationship between data sets and certain data characteristics may be difficult to predict. Notably, in the case of medical order data sets, the relationship between the medical orders and certain characteristics are not static over time, and therefore not predictable with a static model. In other words, existing static data models cannot predictably determine certain characteristics of medical orders over time. The reason that static data models cannot determine these characteristics is because conditions of medical orders change frequently, altering the relationships between elements of medical orders and related characteristics. Nevertheless, it is crucial that medical order processing systems determine some of these characteristics as early as possible in the information cycle of processing the medical order.

In the context of prescription medical orders, one characteristic that is particularly important is the determination of whether a medical order is prior authorized. Prior authorization (PA) is a characteristic that indicates whether authorization is required from a health care insurer (or payer) after a physician prescribes a drug for a patient. Determining whether a medical order requires PA plays an essential role in accurate, effective, and timely processing of prescription medical orders. As such, in medical order systems, determining whether a medical order requires PA is crucial for successful processing of orders. In known systems, determination of whether a medical order requires PA cannot be completed because PA information is typically not explicitly provided. Instead, estimates of whether a medical order requires PA can be made based on other order characteristics prior to order processing. However, as noted, whether a medical order requires PA cannot be predictably determined with static models. As a result, using known systems, medical order systems are faced with a fundamental dilemma—an unacceptable delay in the processing of the medical order or a risk of improper medical order processing.

Therefore, in existing medical prescription processing systems, incorrect or improper authorization rule models may be used, causing the systems to create erroneous results and improper results. In some examples, the systems can only be improved through the use of manual verification steps, reversal of orders, or cancellation of orders. Even with such improvements, the risk of erroneous and improper results remains.

As such, prescription processing systems capable of predicting whether a medical order requires prior authorization, prior to order processing, are desirable.

BRIEF SUMMARY OF THE INVENTION

In one aspect, a machine learning system for training a data model to predict data states is provided. In the example embodiment, the machine learning system is configured to train a data model to predict whether a medical order requires prior authorization ("PA") for medical orders within a medical order data set so that related systems may process incoming medical orders with PA requirement determinations as predicted by the data model. The machine learning system includes a first data warehouse system. The first data warehouse system includes a first processor and a first memory. The first data warehouse system further includes one or more historical orders and one or more payer responses. Each of the historical orders is associated with one of the payer responses. The machine learning system also includes a first prescription processing system (alternatively described as a prescription processing system, or a prescription processing computing device) that is in communication with the first data warehouse system. The prescription processing system includes a second processor and a second memory. Using the second processor, the first prescription processing system is configured to perform at least the following steps: (a) receive a first portion of the historical orders and a first portion of the payer responses; (b) apply at least one data balancing operation to the first portion of the historical orders and the first portion of the payer responses; (c) generate a data model of the first portion of the historical orders and the first portion of the payer responses, wherein the data model is substantially represented by a tree-structure including one or more leaves; (d) apply a predictive machine learning model to the data model to generate a trained predictor of a whether a medical order requires PA, associated with order data; (e) receive one or more production orders; (f) apply the trained predictor to the production orders to determine whether the medical order requires PA for each of the production orders; and (g) process the production orders with each determination of whether the medical order requires PA.

In another aspect, a method for training a data model to predict data states is provided. In the example embodiment, the method is used to train a data model to predict whether a medical order requires prior authorization ("PA") for medical orders within a medical order data set so that the prescription processing system and related systems may process incoming medical orders with PA requirement determinations as predicted by the data model. The method is performed by a first prescription processing system included within a machine learning system. In the example embodiment, the first prescription processing system is in communication with a data warehouse system that is included within the machine learning system. The first data warehouse system includes one or more historical orders and one or more payer responses. Each of the historical orders is associated with one of the payer responses. The prescription processing system includes a processor and a memory. The method performed by the prescription processing system includes at least the following steps: (a) receive a first portion of the historical orders and a first portion of the payer responses; (b) apply at least one data balancing operation to the first portion of the historical orders and the first portion of the payer responses; (c) generate a data model of the first portion of the historical orders and the first portion of the payer responses, wherein the data model is substantially represented by a tree-structure including one or more leaves; (d) apply a predictive machine learning model to the data model to generate a trained predictor of whether a medical order requires PA, associated with order data; (e) receive one or more production orders; (f) apply the trained predictor to the production orders to determine whether the medical order requires PA for each of the production orders; and (g) process the production orders with each determination of whether the medical order requires PA.

In yet another aspect, a prescription processing system used for training a data model to predict data states is provided. In the example embodiment, the prescription processing system trains a data model to predict whether a medical order requires prior authorization ("PA") for medical orders within a medical order data set so that the prescription processing system and related systems may process incoming medical orders with PA requirement determinations as predicted by the data model. In the example embodiment, the prescription processing system is included within a machine learning system. The prescription processing system is in communication with a data warehouse system that is also included within the machine learning system. The data warehouse system includes one or more historical orders and one or more payer responses. Each of the historical orders is associated with one of the payer responses. The prescription processing system includes a processor and a memory. The prescription processing system is configured to perform at least the following steps: (a) receiving a first portion of the historical orders and a first portion of the payer responses; (b) applying at least one data balancing operation to the first portion of the historical orders and the first portion of the payer responses; (c) generating a data model of the first portion of the historical orders and the first portion of the payer responses, wherein the data model is substantially represented by a tree-structure including one or more leaves; (d) applying a predictive machine learning model to the data model to generate a trained predictor of whether a medical order requires PA, associated with order data; (e) receiving one or more production orders; (f) applying the trained predictor to the production orders to determine whether the medical order requires PA for each of the production orders; and (g) processing the production orders with each determination of whether the medical order requires PA.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

In the drawings, reference numbers may be reused to identify similar and/or identical elements.

DETAILED DESCRIPTION

Figure 1:
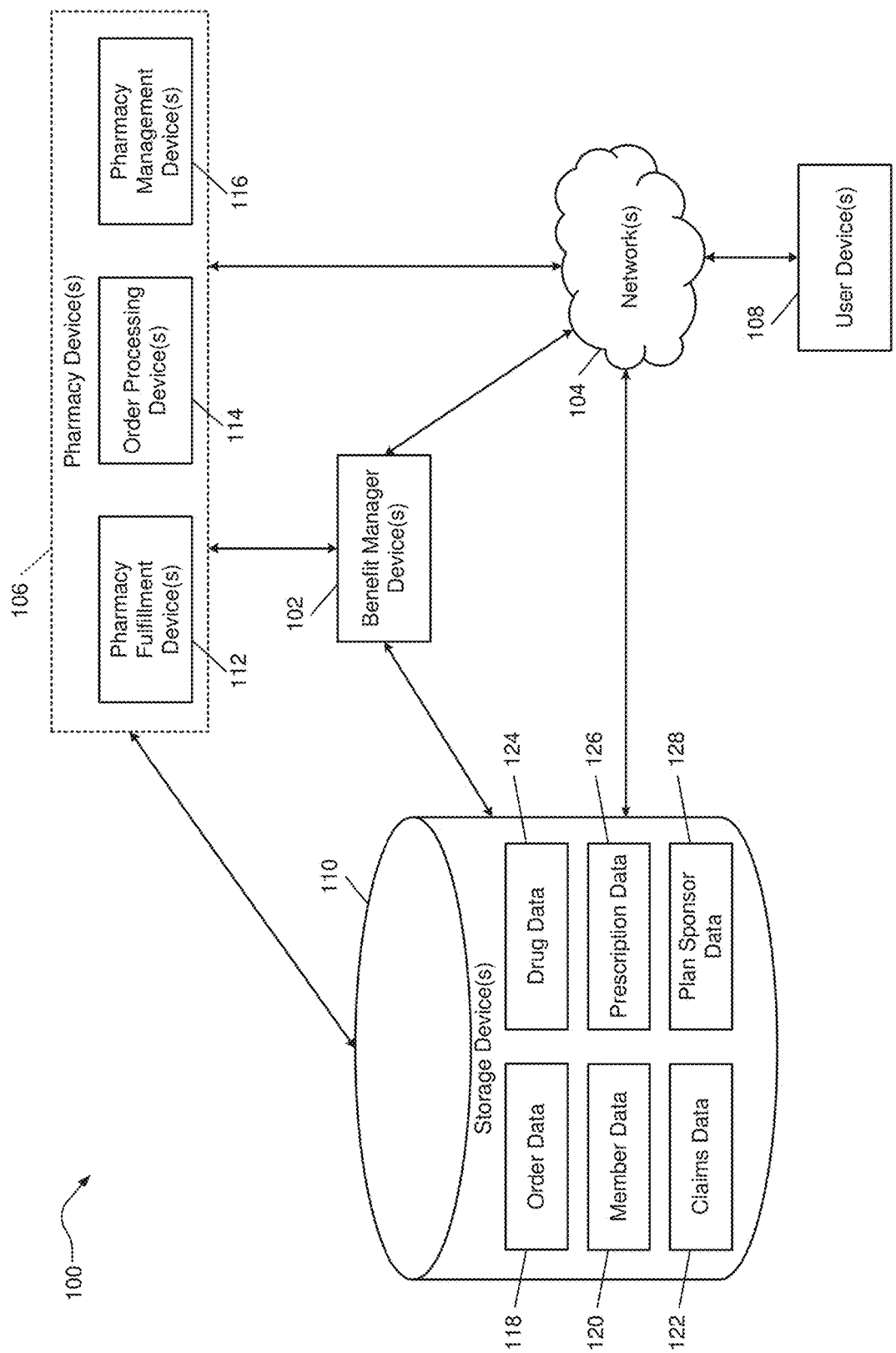
FIG. 1 is a functional block diagram of an example system including a high-volume pharmacy.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As used herein, the term "feature selection" refers to the process of selecting a subset of relevant features (e.g., variables or predictors) that are used in the machine learning system to define data models. Feature selection may alternatively be described as variable selection, attribute selection, or variable subset selection. The feature selection process of the machine learning system described herein allows the prescription processing system to simplify models to make them easier to interpret, reduce the time to train the systems, reduce overfitting, enhance generalization, and avoid problems in dynamic optimization.

As used herein, the term "random forest algorithm" refers to an ensemble learning algorithm used for classification, regression and other tasks. The random forest algorithm operates by constructing one or more of decision trees at the time of training a machine, and outputting the class that is the mode of the classes, or mean prediction of the individual trees to determine the classification or regression, respectively.

As used herein, the term "nearest neighbor algorithm" (also known as "k-nearest neighbor algorithm") refers to a non-parametric method used for classification and regression. In both cases, the input consists of the k closest training examples in the feature space. Like the random forest algorithm, nearest neighbor algorithm may be used for classification or regression and may determine a class membership or object property value, respectively. Generally, the nearest neighbor algorithm involves assigning greater weight to the contributions of the nearer neighbors, so that the nearer (or proximate) neighbors contribute more to the average than the more distant ones. In one example, each neighbor is assigned a weight of 1/d, where d is the distance to the neighbor, and where the weight of the neighbor is thus inverse to the distance from the neighbor.

As used herein, the term "naïve Bayesian algorithm" refers to a probabilistic classifier or regression that utilizes Bayes's theorem and applies naïve (or strong) independence assumptions between the features. Bayes's theorem can be stated as follows:

$$P(A|B) = \frac{P(B|A)P(A)}{P(B)},$$

where A and B are events and P(B)≠0. Like the random forest algorithm and the nearest neighbor algorithm, the naïve Bayesian algorithm may be used for classification or regression.

As used herein, the term "logistic regression algorithm" refers to a method of estimating the parameters of a logistic model. A logistic model uses a logistic function to model at least one binary dependent variable.

As used herein, the term "Principal Component Analysis" or "PCA" refers to a statistically based method of identifying features. Generally, PCA involves the use of orthogonal transformation to convert a set of observations of possibly correlated variables into a set of values of linearly uncorrelated variables known as the "principal components". If there are n observations with p variables, then the number of distinct principal components is (n−1, p). This transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors (each being a linear combination of the variables and containing n observations) are an uncorrelated orthogonal basis set. PCA is sensitive to the relative scaling of the original variables.

The machine learning systems and methods described herein are configured to address known technological problems confronting computing systems and networks that process data sets, specifically the lack of known static relationships between data sets and certain data characteristics. The machine learning systems and methods described are configured to address these known problems particularly as they relate to determining whether a medical order requires PA in medical order data sets. As described above, in existing medical prescription processing systems, incorrect or improper authorization rule models may be used, causing the systems to create erroneous results and improper results because whether a medical order requires PA cannot be accurately determined. In some examples, the systems can only be improved through the use of manual verification steps, reversal of orders, or cancellation of orders. Yet, even when these steps are taken, whether a medical order requires PA cannot be accurately and reliably determined.

The machine learning systems and methods described overcome known deficiencies in previous technological approaches. Using previous approaches, static data models are typically rendered inaccurate when changes were made to payer rules and authorization rules. Such data models could also be rendered inaccurate when new categories of groups and payers were added, when new drugs and drug categories were added, and when diagnosis codes (e.g., ICD10) were changed.

By contrast, the machine learning systems and methods provided allow the prescription processing system to adjust to changes in known environmental conditions without requiring manual verification of whether a medical order requires PA. For example, in some situations, partially incorrect patient policy data or rejection codes may be provided by payers. The machine learning systems and methods described can process medical order data containing such partially incorrect or incomplete data, and still return accurate determinations of whether a medical order requires PA. As such these machine learning systems and methods solve a technological problem related to incomplete and/or unpredictable data (i.e., determinations of whether a medical order requires PA) that cannot be otherwise resolved using known methods and technologies. In particular, the proposed approach of machine learning using a composite multi-algorithm approach to train a trained predictor is a significant technological improvement in the technological field of data sciences. Further, the proposed approach includes active re-training to ensure predictive accuracy. This approach also allows for re-training of the trained predictor as it is used. In this manner, the disclosed machine learning methods and systems prevent the data model and trained predictor from becoming static or stale and therefore possibly prone to error.

Therefore, to overcome known problems of determining whether a medical order requires PA based on other prescription order characteristics, a machine learning system is provided. The machine learning system is capable of performing predictive modeling of prescription order characteristics. Once the machine learning system is trained, the predictive models it generates accurately predict whether a medical order requires PA in incoming prescription orders. In the example embodiment, the machine learning system includes at least a prescription processing system and a data warehouse containing a prescription order database. The prescription processing system is configured to communicate with the data warehouse.

The prescription processing system receives one or more historical orders (or historical medical claims) from the prescription order database included in the data warehouse. Each of the historical orders includes one or more data features. The data features may include defined attributes including payer identifier, therapy identifier, prescription identifier, patient identifier, procedure identifier, diagnosis identifier, policy identifier, prescription group identifier, and drug identifier. The prescription processing system also receives known historical payer responses from the data warehouse. Historical payer responses include data points associated with previous payer responses to medical orders including, without limitation, historical order numbers, historical order timestamp, historical order therapy code, historical order therapy identifier, historical order patient diagnosis information, rejection codes, rejection amounts (if applicable), authorized amounts (if applicable), quantity dispensed, payment details (i.e., the amount that was paid for a given order), and patient responsibility (if applicable). In some examples, PA requirement information may be partially available. In some examples, the data features correspond to the historical payer responses. In other examples, the machine learning system is capable of processing historical payer responses that do not correspond (or do not fully correspond) to the historical payer responses.

In the example embodiment, the historical data is provided to the prescription processing system in batches on a staged basis, such that the prescription processing system learns from each batch. Specifically, the historical data is moved from a machine learning staging table to a machine learning target table. After the historical data is moved, the prescription processing system verifies that each record of the historical data does not already exist in the prescription processing system data records. The prescription processing system uses the machine learning target table to learn from the verified unique data records.

The prescription processing system performs initial pre-processing on the historical orders to clean the data by, for example, removing erroneous historical orders and duplicative historical orders. The prescription processing system identifies duplicative historical orders by scanning the historical orders with overlapping data features and overlapping time stamps. The prescription processing system identifies erroneous historical records by comparing the values of certain data features to known value options.

After preprocessing, the prescription processing system performs a feature selection (or feature extraction) on the historical orders to sample at least one of the data features for each of the historical orders. The feature selection process may use a dimensionality reduction process known as Principal Component Analysis ("PCA").

Alternatively, the feature selection process may use the random forest algorithm to identify important features. A random forest is an ensemble method that uses a group of decision trees at the time that the machine is trained, and outputs the class that is most characteristic of the classes.

The prescription processing system also performs a data balancing operation on the historical orders. The data balancing operation involves adjusting the proportions of certain subsets of the historical data in order to train the machine learning data model. In one example, the data balancing operation incorporates distorting the historical orders by selecting out a subset of historical orders with known PA states. In another example, the data balancing operation incorporates distorting the historical orders by creating duplicates of the subset of historical orders with unknown PA states. The prescription processing system also performs the data balancing operation by providing greater weight to the lowest occurrences of data that are determined to be significant to the model based on feature selection.

The prescription processing system trains a predictive machine learning model with the historical orders and the historical payer responses to make a first prediction of the PA state. Specifically, the prescription processing system creates a data model based on the historical orders, and the historical payer responses, that defines a tree-structure descriptive of the historical orders and further describing the associated data features of the historical orders.

The prescription processing system trains the predictive machine learning model using a combination of a) a nearest neighbor algorithm configured to consider the nearest twenty neighbors, b) a logistic regression algorithm, c) a random forest algorithm, and d) a naïve Bayesian algorithm. This combination of algorithms provides unexpected results for predicting the PA state with a high degree of accuracy.

After the prescription processing system trains the predictive machine learning model, it receives a second plurality of historical orders and a second set of historical payer responses. The prescription processing system applies the trained predictive machine learning model to the second plurality of historical orders to identify a predicted PA requirement associated with each of the second plurality of historical orders. (In the example embodiment, the predicted PA requirement, and the actual PA requirement, is either true or false.) The prescription processing system compares the predicted PA requirement determined by the trained predictive machine learning model to the actual PA requirement indicated in the historical payer responses. The prescription processing system identifies each discrepancy between a predicted PA requirement and the actual PA requirement for each of the second plurality of historical orders. The prescription processing system further determines an error rate for the trained predictive machine learning model based on the identified discrepancies.

The prescription processing system receives a pre-defined threshold for PA requirement predictive accuracy. If the error rate exceeds the pre-defined threshold, the prescription processing system re-trains the predictive machine learning model by training the trained predictive machine learning model to the second plurality of historical orders and the second set of historical payer responses. In such examples, the prescription processing system further receives a third plurality of historical orders and a third set of historical payer responses and tests the re-trained predictive machine learning model using the third plurality of historical orders and the third set of historical payer responses.

The prescription processing system iteratively re-trains the predictive machine learning model until the trained (or re-trained) model has an error rate that falls below the pre-defined threshold, and is therefore sufficiently accurate. The prescription processing system receives production order data and makes determinations of whether a medical order requires PA using the trained (or re-trained) model. The prescription processing system may also continue to iteratively re-train the predictive machine learning model on additional historical orders and additional historical payer responses.

Generally, the systems and methods described herein are configured to perform at least the following steps: (a) receive a first portion of the historical orders and a first portion of the payer responses; (b) apply at least one data balancing operation to the first portion of the historical orders and the first portion of the payer responses; (c) generate a data model of the first portion of the historical orders and the first portion of the payer responses, wherein the data model is substantially represented by a tree-structure including one or more leaves; (d) apply a predictive machine learning model to the data model to generate a trained predictor of whether a medical order requires PA, associated with order data; (e) receive one or more production orders; (f) apply the trained predictor to the production orders to determine whether a medical order requires PA for each of the production orders; (g) process the production orders with each associated determination of whether the medical order requires PA; (h) apply the predictive machine learning model to the data model, wherein the predictive machine learning model is trained using at least one of a) a nearest neighbor algorithm, b) a logistic regression algorithm, c) a random forest algorithm, and d) a naïve Bayesian algorithm; (i) use the nearest neighbor algorithm to consider a set of neighbors including the nearest twenty neighbors identified for each of the leaves of the tree-structure; (j) receive a second portion of the historical orders and a second portion of the payer responses; (k) apply the trained predictor to the second portion of the historical orders to determine whether a medical order requires PA for each of the second portion of the historical orders; (l) receive a pre-defined threshold for error; (m) determine an error rate for the trained predictor by comparing the determined PA requirement for each of the second portion of the historical orders to the associated second portion of the payer responses; (n) determine whether the trained predictor requires re-training; (o) upon determining that the trained predictor requires re-training, re-train the trained predictor by generating a second data model of the second portion of the historical orders and the second portion of the payer responses, wherein the second data model is substantially represented by a tree-structure including one or more leaves, and applying a predictive machine learning model to the second data model to generate a re-trained predictor of whether a medical order requires PA, associated with order data; (p) receive a third portion of the historical orders and a third portion of the payer responses; (q) apply the re-trained predictor to the third portion of the historical orders to determine whether a medical order requires PA for each of the third portion of the historical orders; (r) receive the pre-defined threshold for error; (s) determine a second error rate for the re-trained predictor by comparing the determined PA requirement for each of the third portion of the historical orders to the associated third portion of the payer responses; (t) re-balance the first portion of the historical orders and the first portion of the payer responses; (u) receive additional historical orders and additional historical payer responses; and (v) iteratively re-train the trained predictor on the additional historical orders and the additional historical payer responses in parallel with the use of the trained predictor.

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104.

The system 100 may also include one or more user device(s) 108. A user, such as a pharmacist, patient, data analyst, health plan administrator, etc., may access the benefit manager device 102 or the pharmacy device 106 using the user device 108. The user device 108 may be a desktop computer, a laptop computer, a tablet, a smartphone, etc.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in a storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
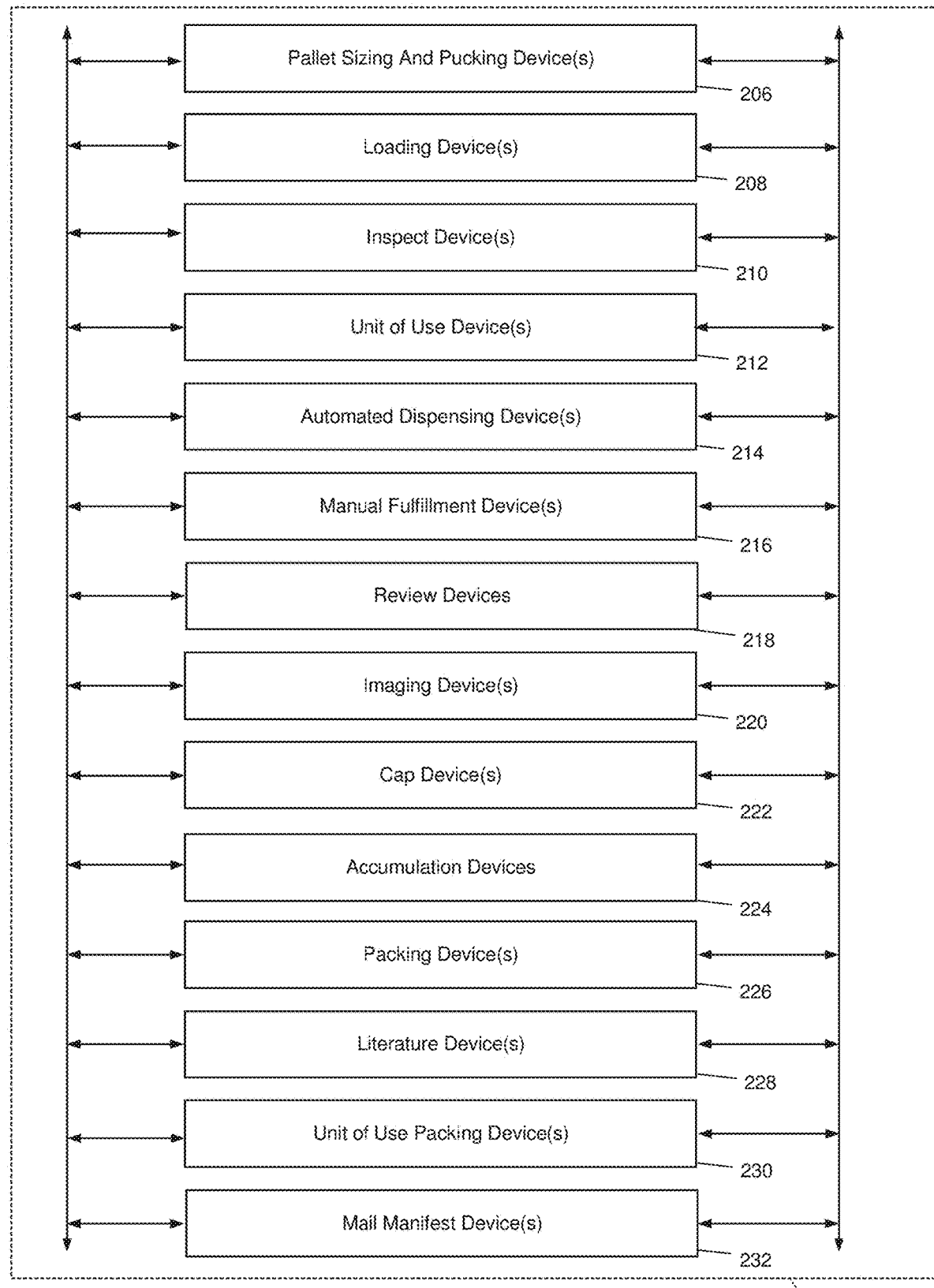
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
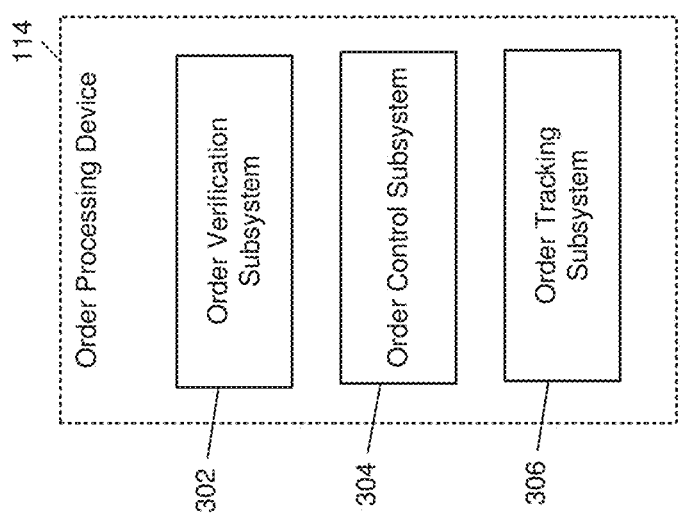
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may include order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Figure 4:
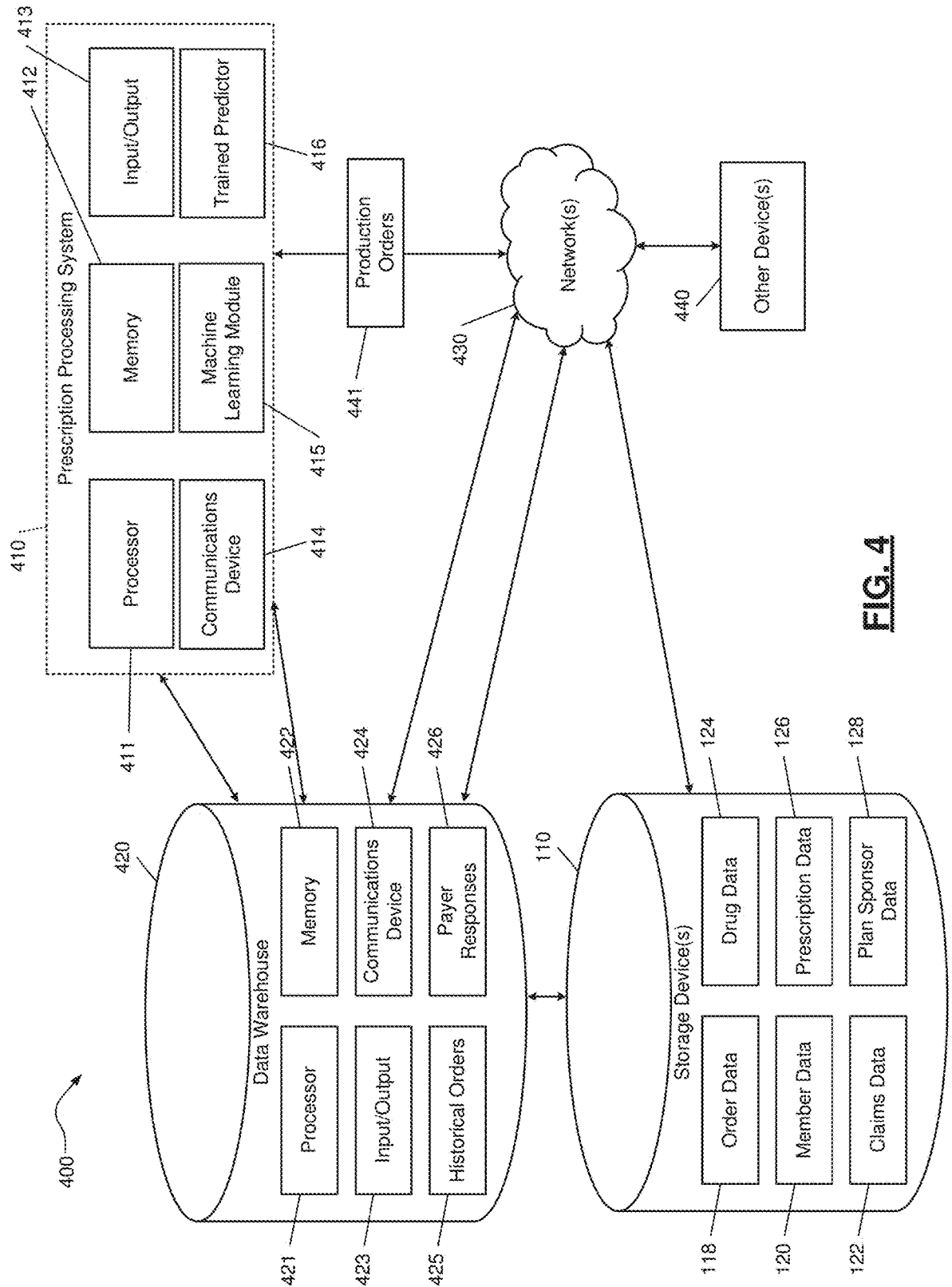
FIG. 4 is a functional block diagram of a machine learning system that may be deployed within the system of FIG. 1.

FIG. 4 illustrates a functional block diagram of a machine learning system 400 that may be deployed within, or as a variation of, the system of FIG. 1. As shown, storage device 110 is in communication with the components of machine learning system 400. Machine learning system 400 includes a prescription processing system 410 which further includes a processor 411, a memory 412, an input/output 413, a communications device 414, a machine learning module 415, and a trained predictor 416. Exemplary attributes of components 411, 412, 413, and 414 are further described in FIG. 5 with respect to exemplary corresponding components 511, 512, 513, and 514, respectively.

Machine learning system 400 also includes a data warehouse 420 which further includes a processor 421, a memory 422, an input/output 423, a communications device 424, a set of historical orders 425, and a set of payer responses 426. Exemplary attributes of components 421, 422, 423, and 424 are further described in FIG. 5 with respect to exemplary corresponding components 511, 512, 513, and 514, respectively. In some examples, data warehouse is alternatively included within prescription processing system 410 or vice versa. In further examples, data warehouse 420 and prescription processing system 410 are included within other devices including, for example, other devices 440.

Data warehouse 420 is substantially in communication (via any suitable form) with storage device 110 and the data elements order data 118, member data 120, claims data 122, drug data 124, prescription data 126, and plan sponsor data 128. Further, via at least network 430, all components of machine learning system 400 are capable of retrieving data from and writing data to storage device 110. As indicated and described herein, historical orders 425 and payer responses 426 relate to data within storage device 110 including at least order data 118, member data 120, claims data 126, and plan sponsor data 128. Moreover, data reflected in machine learning system 400 including production orders 441 may be retrieved from, or be substantially represented in, storage device 110. In at least some examples, machine learning system 400 creates or retrieves necessary data from storage device 110.

Machine learning system 400 also may include other devices 440 that allow access any system of machine learning system 400 directly or indirectly. In the example embodiment, other devices 440 includes order systems that are capable of providing and transmitting current prescription orders to the machine learning system 400. Machine learning system 400 further includes a network 430 that is configured to provide communication between the systems 410, 420, and 440 of machine learning system 400, and from and to external devices (not shown).

In the example embodiment, prescription processing system 410 receives a first portion of the historical orders 425 and a first portion of the payer responses 426 from data warehouse 420. Prescription processing system 410 further applies at least one data balancing operation to the first portion of the historical orders 425 and the first portion of the payer responses 426.

In some examples, prescription processing system 410 is configured to further pre-process data before training the trained predictor 416 by re-balancing the first portion of the historical orders 425 and the first portion of the payer responses 426.

Prescription processing system 410 further generates a data model of the first portion of the historical orders 425 and the first portion of the payer responses 426, wherein the data model is substantially represented by a tree-structure including one or more leaves. Prescription processing system 410 applies a predictive machine learning model 415 to the data model to generate a trained predictor of whether a medical order requires PA 416 ("trained predictor") associated with order data 425 and 426.

In the example embodiment, prescription processing system 410 applies the predictive machine learning model 415 to the data model using a combination of algorithms. In the exemplary embodiment, the combination of algorithms includes at least one of a) a nearest neighbor algorithm, b) a logistic regression algorithm, c) a random forest algorithm, and d) a naïve Bayesian algorithm. In at least some embodiments, when the predictive machine learning model 415 is applied, the nearest neighbor algorithm is configured to consider a set of neighbors including the nearest twenty neighbors identified for each of the leaves of the tree-structure. In some example embodiments, the combination of algorithms includes any combination or permutation including a) a nearest neighbor algorithm, b) a logistic regression algorithm, c) a random forest algorithm, and/or d) a naïve Bayesian algorithm.

In some embodiments, prescription processing system 410 is configured to also receive a second portion of the historical orders 425 and a second portion of the payer responses 426. In such embodiments, prescription processing system 410 is also configured to apply the trained predictor 416 to the second portion of the historical orders 425 to determine whether a medical order requires PA for each of the second portion of the historical orders 425. Prescription processing system 410 also receives a pre-defined threshold for error and determines an error rate for the trained predictor 416 by comparing the determined PA requirement for each of the second portion of the historical orders 425 to the associated second portion of the payer responses 426. Based on the determined error rate and the pre-defined threshold for error, prescription processing system 410 determines whether the trained predictor 416 requires re-training.

When prescription processing system 410 determines that trained predictor 416 requires retraining, prescription processing system 410 is configured to perform such retraining. Prescription processing system 410 accomplishes this by generating a second data model of the second portion of the historical orders 425 and the second portion of the payer responses 426. The second data model is substantially represented by a tree-structure including one or more leaves. Prescription processing system 410 applies a predictive machine learning model to the second data model to generate a re-trained predictor of whether a medical order requires PA associated with production orders 441. The re-trained predictor replaces trained predictor 416. Prescription processing system 410 receives a third portion of the historical orders 425 and a third portion of the payer responses 426 and applies the re-trained predictor (now trained predictor 416) to the third portion of the historical orders 425 to determine whether a medical order requires PA for each of the third portion of the historical orders 425. Prescription processing system 410 receives the pre-defined threshold for error and determines a second error rate for the re-trained predictor (now trained predictor 416) by comparing the determined PA requirement for each of the third portion of the historical orders 425 to the associated third portion of the payer responses 426.

In additional examples, prescription processing system 410 is configured to receive additional historical orders 425 and additional historical payer responses 426 and iteratively re-train the trained predictor 416 on the additional historical orders 425 and the additional historical payer responses 426 in parallel with the use of the trained predictor 416. This approach allows the system to utilize the benefits of the trained predictor 416 while actively updating it to ensure that changes in external conditions are timely captured and used for re-training. In this way, the prescription processing system 410 can ensure that the data models and trained predictor 416 do not become static or stale, and instead reflect changes in the relationship between medical order data sets and whether a medical order requires PA.

Once trained predictor 416 is trained (or retrained, as needed) to accurately predict whether a medical order requires PA, prescription processing system 410 receives one or more production orders 441 from an order system such as other devices 440. Prescription processing system 410 is configured to apply the trained predictor 416 to the production orders to determine whether a medical order requires PA for each of the production orders 441 process the production orders with each associated PA requirement determination. As a result of this step, prescription processing system 410 can ensure that an accurate determination of whether a medical order requires PA can be determined for each received production order 441.

Figure 5:
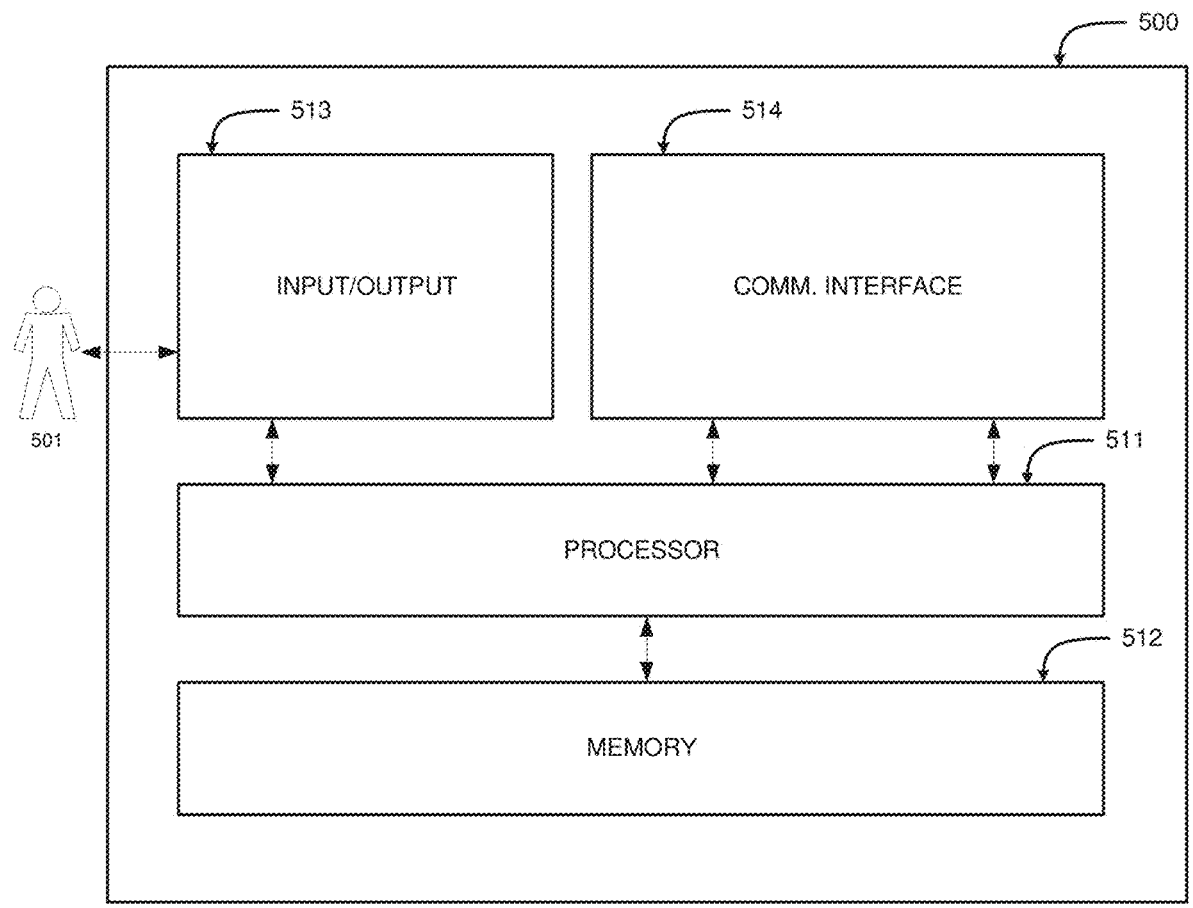
FIG. 5 is a functional block diagram of an example computing device that may be used in the system architecture of FIG. 4.

FIG. 5 is a functional block diagram of an example computing device 500 that may be used in the system architecture of FIG. 4. Specifically, computing device 500 illustrates an exemplary configuration of a computing device such as prescription processing system 410, data warehouse 420, or other devices 440. Computing device 500 illustrates an exemplary configuration of a computing device operated by a user 501 in accordance with one embodiment of the present invention. Computing device 500 may include, but is not limited to, prescription processing system 410, data warehouse 420, other devices 440, other user systems, and other server systems. Computing device 500 may also include pharmacy devices 106 including pharmacy fulfillment devices 112, order processing devices 114, and pharmacy management devices 116, storage devices 110, benefit manager devices 102, and user devices 108 (all shown in FIG. 1), mobile computing devices, stationary computing devices, computing peripheral devices, smart phones, wearable computing devices, medical computing devices, and vehicular computing devices. Alternatively, computing device 500 may be any computing device capable of the machine learning methods for predicting whether a medical order requires PA described herein. In some variations, the characteristics of the described components may be more or less advanced, primitive, or non-functional.

In the exemplary embodiment, computing device 500 includes a processor 511 for executing instructions. In some embodiments, executable instructions are stored in a memory area 512. Processor 511 may include one or more processing units, for example, a multi-core configuration. Memory area 512 is any device allowing information such as executable instructions and/or written works to be stored and retrieved. Memory area 512 may include one or more computer readable media.

Computing device 500 also includes at least one input/output component 513 for receiving information from and providing information to user 501. In some examples, input/output component 513 may be of limited functionality or non-functional as in the case of some wearable computing devices. In other examples, input/output component 513 is any component capable of conveying information to or receiving information from user 501. In some embodiments, input/output component 513 includes an output adapter such as a video adapter and/or an audio adapter. Input/output component 513 may alternatively include an output device such as a display device, a liquid crystal display (LCD), organic light emitting diode (OLED) display, or "electronic ink" display, or an audio output device, a speaker or headphones. Input/output component 513 may also include any devices, modules, or structures for receiving input from user 501. Input/output component 513 may therefore include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output and input device of input/output component 513. Input/output component 513 may further include multiple sub-components for carrying out input and output functions.

Computing device 500 may also include a communications interface 514, which may be communicatively coupleable to a remote device such as a remote computing device, a remote server, or any other suitable system. Communication interface 514 may include, for example, a wired or wireless network adapter or a wireless data transceiver for use with a mobile phone network, Global System for Mobile communications (GSM), 3G, 4G, or other mobile data network or Worldwide Interoperability for Microwave Access (WIMAX). Communications interface 514 is configured to allow computing device 500 to interface with any other computing device or network using an appropriate wireless or wired communications protocol such as, without limitation, BLUETOOTH®, Ethernet, or IEE 802.11. Communications interface 514 allows computing device 500 to communicate with any other computing devices with which it is in communication or connection.

Figure 6:
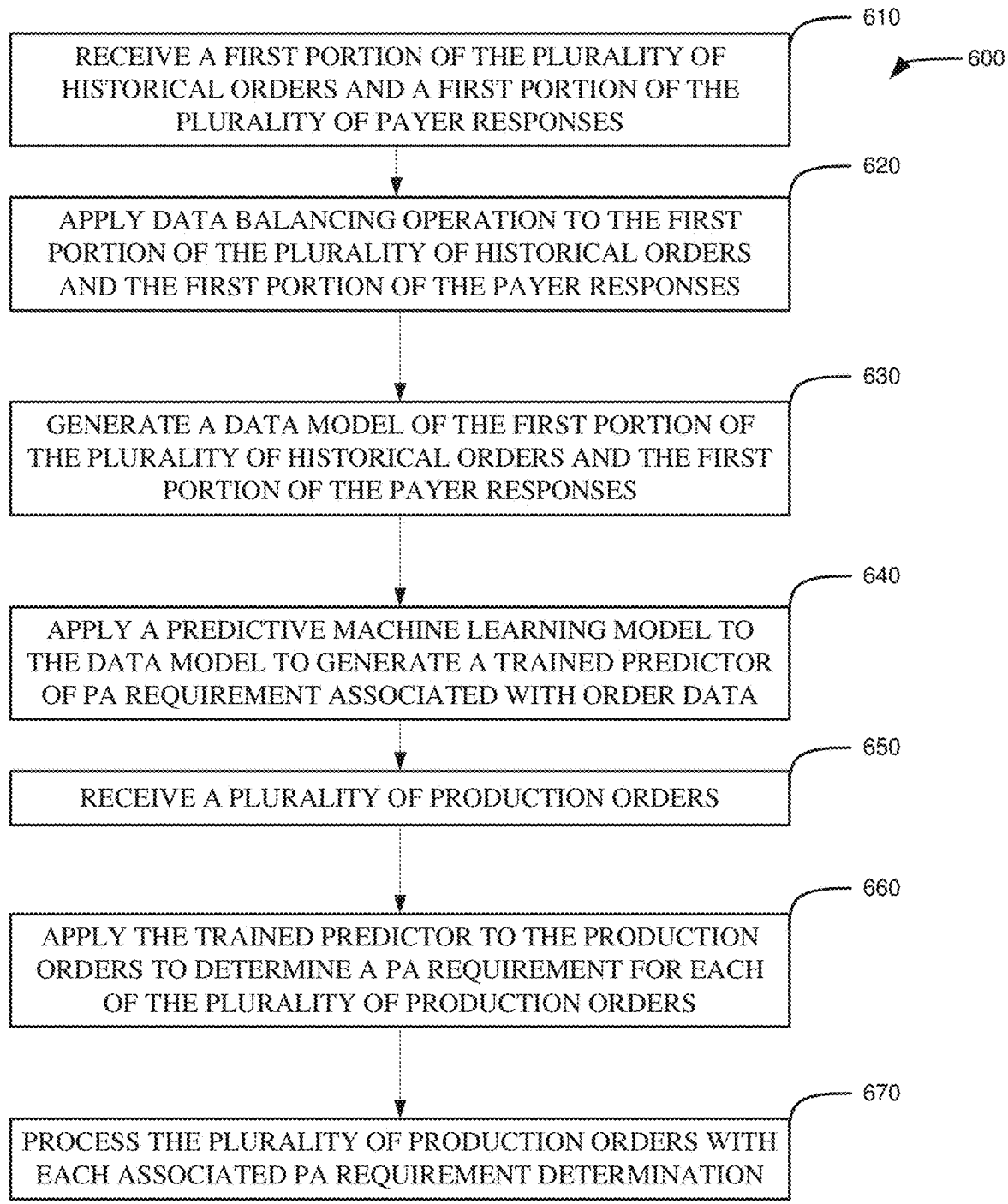
FIG. 6 is a flow diagram representing the analytics process from the perspective of the prescription processing system or prescription processing computing device shown in FIG. 5.

FIG. 6 is a flow diagram 600 representing the analytics process from the perspective of the prescription processing system 410 or prescription processing computing device shown in FIG. 4. Flow diagram 600 depicts the exemplary steps that are executed by prescription processing system 410 to train trained predictor 416 (shown in FIG. 4) and predict the PA states of production orders 441 (shown in FIG. 4).

In the example embodiment, prescription processing system 410 receives 610 a first portion of the historical orders 425 and a first portion of the payer responses 426 from data warehouse 420 (all shown in FIG. 4). Prescription processing system 410 applies 620 at least one data balancing operation to the first portion of the historical orders 425 and the first portion of the payer responses 426. Prescription processing system 410 generates 630 a data model of the first portion of the historical orders 425 and the first portion of the payer responses 426, wherein the data model is substantially represented by a tree-structure including one or more leaves.

Prescription processing system 410 also applies 640 a predictive machine learning model to the data model to generate a trained predictor 416 (shown in FIG. 4) of whether a medical order requires PA associated with production order data 441. Prescription processing system 410 also receives 650 one or more production orders 441 including production data for prescription orders that may not include information regarding whether a medical order requires PA.

Prescription processing system 410 applies 660 trained predictor 416 to the production orders 441 to determine whether a medical order requires PA for each of the production orders 441. Prescription processing system 410 processes 670 the production orders 441 with each associated PA determination as determined by trained predictor 416.

Figure 7:
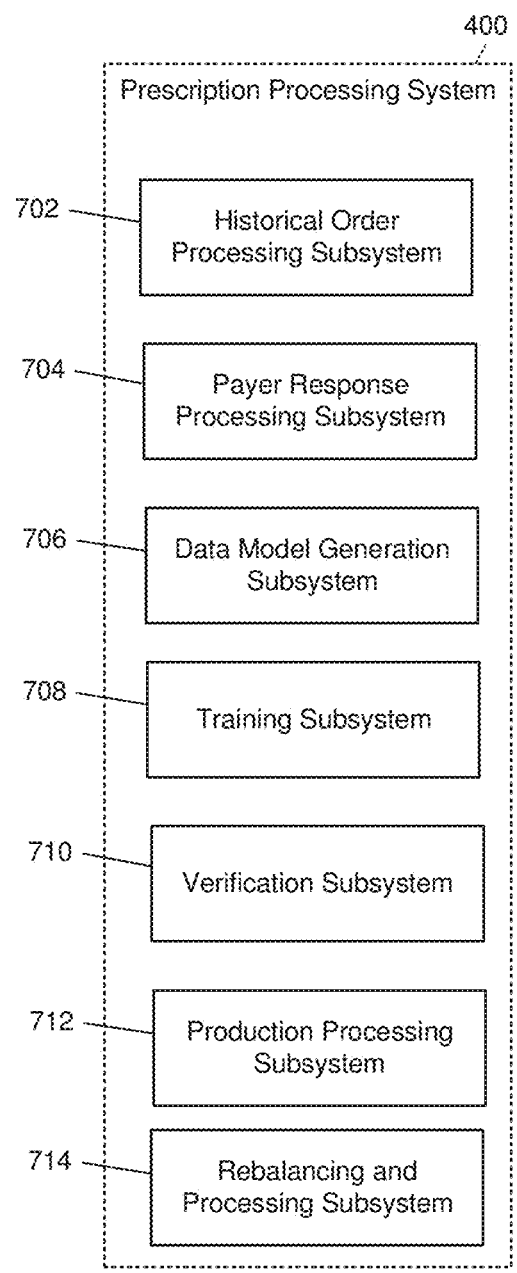
FIG. 7 is a diagram of elements of one or more example computing devices that may be used in the system shown in FIGS. 1 and 4.

FIG. 7 is a diagram of elements of one or more example computing devices that may be used in the system shown in FIGS. 1 and 4. Specifically, FIG. 7 describes subsystems available to machine learning system 400 that are capable of providing the functionality described herein. Machine learning system 400 includes historical order processing subsystem 702 that is configured to receive, process, manage, and transport historical orders 425 within machine learning system 400 and to prescription processing system 410. Machine learning system 400 includes payer response processing subsystem 704 that is configured to receive, process, manage, and transport payer responses 426 within machine learning system 400 and to prescription processing system 410. Using historical order processing subsystem 702 and payer response processing subsystem 704, machine learning system 400 is configured to maintain relationships between entries and records for historical orders 425 and payer responses 426 within data warehouse 420. Historical order processing subsystem 702 and payer response processing subsystem 704 are also configured to provide a first portion of the historical orders 425 and a first portion of the payer responses 426 to prescription processing system 410.

Machine learning system 400 also includes data model generation subsystem 706. Data model generation subsystem 706 is configured to at least generate data models of the first portion of the historical orders 425 and the first portion of the payer responses 426, wherein the data model is substantially represented by a tree-structure including one or more leaves. Data model generation subsystem 706 is also configured to generate a second data model of the second portion of the historical orders 425 and the second portion of the payer responses 426, wherein the second data model is substantially represented by a tree-structure including one or more leaves.

Machine learning system 400 also includes training subsystem 708 which is configured to at least apply a predictive machine learning model to the data model to generate a trained predictor of whether a medical order requires PA associated with order data. Training subsystem 708 substantially represents machine learning module 415. Training subsystem 708 is also configured to apply the predictive machine learning model to the data model (generated by data model generation subsystem 706). The training subsystem 708 may train the predictive machine learning model using a composite algorithm of a) a nearest neighbor algorithm, b) a logistic regression algorithm, c) a random forest algorithm, and d) a naïve Bayesian algorithm. In some examples, the training subsystem 708 configures the nearest neighbor algorithm to consider a set of neighbors including the nearest twenty neighbors identified for each of the leaves of the tree-structure.

Machine learning system 400 also includes verification subsystem 710 to determine whether the trained predictor 416 is successfully trained. As such, the verification subsystem 710 is configured to verify the trained predictor 416. As such, verification subsystem 710 receives a second portion of the historical orders 425 and a second portion of the payer responses 426 and applies the trained predictor 416 to the second portion of the historical orders 425 to determine whether a medical order requires PA for each of the second portion of the historical orders. Verification subsystem 710 also receives or otherwise determines a pre-defined threshold for error. The pre-defined threshold includes the threshold level of performance required for trained predictor 416. Verification subsystem 710 also determines an error rate for the trained predictor 416 by comparing the determined PA requirement for each of the second portion of the historical orders 425 to the associated second portion of the payer responses 426 and determines whether the trained predictor 416 requires re-training. Verification subsystem 710 determines whether the trained predictor 416 requires re-training by comparing the determined error rate to the pre-defined threshold.

If verification subsystem 710 determines that trained predictor 416 requires retraining, verification subsystem 710 is also configured to re-train the trained predictor by generating a second data model (using data model generation subsystem 706) of the second portion of the historical orders 425 and the second portion of the payer responses 426. The second data model is substantially represented by a tree-structure including one or more leaves. Verification subsystem 710 also causes training subsystem 708 to apply the predictive machine learning model to the second data model to generate a re-trained predictor of whether a medical order requires PA associated with order data 441. Verification subsystem 710 is also configured to receive a third portion of the historical orders 425 and a third portion of the payer responses 426 and apply the re-trained predictor 416 to the third portion of the historical orders 425 to determine whether a medical order requires PA for each of the third portion of the historical orders 425. After such re-training, verification subsystem 710 is configured to receive the pre-defined threshold for error and determine a second error rate for the re-trained predictor 416 by comparing the determined PA requirement for each of the third portion of the historical orders 425 to the associated third portion of the payer responses 426. As such, verification subsystem 710 allows for dynamic updating and re-training of trained predictor 416 to ensure accuracy of the prediction of whether a medical order requires PA.

Machine learning system 400 also includes a processing subsystem 712 which is configured to receive one or more production orders 441, apply the trained predictor 416 to the production orders 441 to determine whether a medical order requires PA for each of the production orders 441, and process the production orders 441 with each associated PA requirement determination.

Machine learning system 400 also includes pre-processing services included within rebalancing and processing subsystem 714. Rebalancing and processing subsystem 714 is configured to perform data balancing functions including, for example, applying at least one data balancing operation to the first portion of the historical orders and the first portion of the payer responses. Rebalancing and processing subsystem 714 is also configured to re-balance the first portion of the historical orders 425 and the first portion of the payer responses 426.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave). The term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A system for determining prior authorization (PA) requirements for prescriptions, the system comprising:
at least one processor; and
at least one memory component having instructions stored thereon, which, when executed by the at least one processor, cause the at least one processor to perform operations comprising:
receiving a first portion of a plurality of historical orders and a first portion of a plurality of payer responses, the plurality of historical orders being associated with respective ones of the plurality of payer responses;
applying at least one data balancing operation to the first portion of the plurality of historical orders and the first portion of the payer responses;
generating a data model of the first portion of the plurality of historical orders and the first portion of the payer responses, the data model being represented by a tree-structure including a plurality of leaves, nodes, and edges;
generating a predictive machine learning model;
applying the predictive machine learning model to the data model to generate a trained predictor of whether a medical order requires prior authorization (PA), associated with order data;
receiving a plurality of prescription production orders;
applying the trained predictor to the plurality of prescription production orders to determine whether the medical order requires a PA for respective ones of the plurality of prescription production orders; and
processing the plurality of prescription production orders with associated PA requirement determinations for the respective ones.

2. The system of claim 1, wherein the operations further comprise:
updating the trained predictor, by:
applying the predictive machine learning model to the data model; and
training the predictive machine learning model using at least one of a) a k-nearest neighbor algorithm, b) a logistic regression algorithm, c) a random forest algorithm, and d) a naive Bayesian algorithm.

3. The system of claim 2, wherein training the predictive machine learning model further comprises:
applying the k-nearest neighbor algorithm, including considering a set of neighbors comprising the nearest twenty neighbors identified for the plurality of leaves of the tree-structure.

4. The system of claim 1, wherein the operations further comprise:
receiving a second portion of the plurality of historical orders and a second portion of the plurality of payer responses;
applying the trained predictor to the second portion of the plurality of historical orders to determine whether a medical order requires PA for the second portion of the plurality of historical orders;
receiving a pre-defined threshold for error;
determining an error rate for the trained predictor by comparing the determined PA requirement for the second portion of the plurality of historical orders to the associated second portion of the plurality of payer responses; and
determining whether the trained predictor requires re-training.

5. The system of claim 4, wherein the operations further comprise:
upon determining that the trained predictor requires re-training,
re-training the trained predictor by generating a second data model of the second portion of the plurality of historical orders and the second portion of the payer responses, the second data model being represented by a tree-structure including a plurality of leaves, and
applying the predictive machine learning model to the second data model to generate a re-trained predictor of whether a medical order requires PA, associated with order data;
receiving a third portion of the plurality of historical orders and a third portion of the plurality of payer responses;
applying the re-trained predictor to the third portion of the plurality of historical orders to determine whether a medical order requires PA for respective ones of the third portion of the plurality of historical orders;
receiving the pre-defined threshold for error; and
determining a second error rate for the re-trained predictor by comparing the determined PA requirement for the respective ones of the third portion of the plurality of historical orders to the associated third portion of the plurality of payer responses.

6. The system of claim 1, wherein the operations further comprise:
re-balancing the first portion of the plurality of historical orders and the first portion of the plurality of payer responses, to create balanced data; and
generating the data model based on the balanced data.

7. The system of claim 1, wherein the operations further comprise:
receiving additional pluralities of historical orders and additional pluralities of historical payer responses; and
iteratively re-training the trained predictor on the additional pluralities of historical orders and the additional pluralities of historical payer responses in parallel with applying the trained predictor to the plurality of prescription production orders.

8. A method for determining prior authorization (PA) requirements for prescriptions, the method comprising:
receiving a first portion of a plurality of historical orders and a first portion of a plurality of payer responses, the plurality of historical orders being associated with respective ones of the plurality of payer responses;
applying at least one data balancing operation to the first portion of the plurality of historical orders and the first portion of the payer responses;
generating a data model of the first portion of the plurality of historical orders and the first portion of the payer responses, the data model being represented by a tree-structure including a plurality of leaves, nodes, and edges;
generating a predictive machine learning model;

applying the predictive machine learning model to the data model to generate a trained predictor of whether a medical order requires prior authorization ("PA") associated with order data;

receiving a plurality of prescription production orders;

applying the trained predictor to the plurality of prescription production orders to determine whether the medical order requires PA for respective ones of the plurality of prescription production orders; and processing the plurality of prescription production orders with associated PA requirement determinations for the respective ones.

9. The method of claim 8, further comprising:

applying the predictive machine learning model to the data model; and training the predictive machine learning model using at least one of a) a k-nearest neighbor algorithm, b) a logistic regression algorithm, c) a random forest algorithm, and d) a naive Bayesian algorithm.

10. The method of claim 9, further comprising:

using the k-nearest neighbor algorithm that is configured to consider a set of neighbors comprising a nearest twenty neighbors identified for respective ones of the plurality of leaves of the tree-structure.

11. The method of claim 8, further comprising:

receiving a second portion of the plurality of historical orders and a second portion of the plurality of payer responses;

applying the trained predictor to the second portion of the plurality of historical orders to determine whether a medical order requires PA for respective ones of the second portion of the plurality of historical orders;

receiving a pre-defined threshold for error;

determining an error rate for the trained predictor by comparing the determined PA requirement for the respective ones of the second portion of the plurality of historical orders to the associated second portion of the plurality of payer responses; and determining whether the trained predictor requires re-training.

12. The method of claim 11, further comprising:

upon determining that the trained predictor requires re-training, re-training the trained predictor by generating a second data model of the second portion of the plurality of historical orders and the second portion of the payer responses, the second data model being represented by a tree-structure including a plurality of leaves, and applying a predictive machine learning model to the second data model to generate a re-trained predictor of whether a medical order requires PA, associated with order data;

receiving a third portion of the plurality of historical orders and a third portion of the plurality of payer responses;

applying the re-trained predictor to the third portion of the plurality of historical orders to determine whether the medical order requires PA for respective ones of the third portion of the plurality of historical orders;

receiving the pre-defined threshold for error; and determining a second error rate for the re-trained predictor by comparing the determined PA requirement for the respective ones of the third portion of the plurality of historical orders to the associated third portion of the plurality of payer responses.

13. The method of claim 8, further comprising re-balancing the first portion of the plurality of historical orders and the first portion of the plurality of payer responses.

14. The method of claim 8, further comprising:

receiving additional pluralities of historical orders and additional pluralities of historical payer responses; and iteratively re-training the trained predictor on the additional pluralities of historical orders and the additional pluralities of historical payer responses in parallel with the use of the trained predictor.

15. A method for determining prior authorization (PA) requirements for prescriptions, the method comprising:

generating a data model of a first portion of a plurality of historical orders and a first portion of a plurality of payer responses, the plurality of historical orders being associated with respective ones of the plurality of payer responses, and the data model being represented by a tree-structure including a plurality of leaves, nodes, and edges;

generating a predictive machine learning model;

iteratively training and re-training a predictor, based on the data model and the predictive machine learning model, to generate a non-static trained predictor;

applying the non-static trained predictor to a plurality of prescription production orders to determine required prior authorizations (PAs) for the plurality of prescription production orders; and processing the plurality of prescription production orders with the required PAs for the plurality of prescription production orders.

16. The method of claim 15, wherein iteratively training and re-training the non-static trained predictor, further comprises:

during a first iteration, applying the predictive machine learning model to the data model to generate an initial trained predictor of whether one of the plurality of prescription production orders requires a PA, the non-static trained predictor comprising the initial trained predictor;

generating a second data model of updated data comprising a second portion of the plurality of historical orders and a second portion of the plurality of payer responses;

during a second iteration, applying the predictive machine learning model to the second data model to generate an updated re-trained predictor based on the updated data; and updating the non-static trained predictor by replacing the initial trained predictor with the updated re-trained predictor.

17. The method of claim 15, further comprising:

ensuring non-static conditions for the predictor and the data model, by:

updating the predictor via timely capture of changes in external conditions; and iteratively re-training the predictor, based on the changes, in parallel with applying the non-static trained predictor to the plurality of prescription production orders.

18. The method of claim 15, further comprising:

prior to generating the data model, applying at least one data balancing operation to the first portion of the plurality of historical orders and the first portion of the payer responses, to create balanced data; and generating the data model using the balanced data.

19. The method of claim 15, further comprising:

establishing a communication connection to a data warehouse system, the data warehouse system including the plurality of historical orders and the plurality of payer responses, the plurality of historical orders being associated with respective ones of the plurality of payer responses;

receiving the first portion of the plurality of historical orders and the first portion of the plurality of payer responses, via the communication connection, to create a set of received data; and generating the data model based on the set of received data.

20. The method of claim 15, further comprising:

updating the predictor, by:
- applying the predictive machine learning model to the data model; and
- training or re-training the predictive machine learning model using at least one of a) a k-nearest neighbor algorithm, b) a logistic regression algorithm, c) a random forest algorithm, and d) a naive Bayesian algorithm.

\* \* \* \* \*